United States Patent
Anderson et al.

(10) Patent No.: US 9,468,773 B1
(45) Date of Patent: Oct. 18, 2016

(54) INTERVENTIONAL MEDICAL SYSTEMS AND IMPLANTABLE MEDICAL DEVICES INCLUDING TETHERING FEATURES, AND ASSOCIATED METHODS

(71) Applicant: Medtronic, Inc., Minneapolis, MN (US)

(72) Inventors: Thomas A Anderson, New Hope, MN (US); Vladimir Grubac, Brooklyn Park, MN (US); Michael C Jacobs, Granger, IN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/706,662

(22) Filed: May 7, 2015

(51) Int. Cl.
| | | |
|---|---|---|
| *A61N 1/00* | (2006.01) | |
| *A61N 1/375* | (2006.01) | |
| *A61N 1/372* | (2006.01) | |
| *A61N 1/362* | (2006.01) | |
| *A61N 1/05* | (2006.01) | |

(52) U.S. Cl.
CPC .............. *A61N 1/3756* (2013.01); *A61N 1/05* (2013.01); *A61N 1/362* (2013.01); *A61N 1/37205* (2013.01)

(58) Field of Classification Search
CPC .... A61N 1/05; A61N 1/362; A61N 1/37205; A61N 1/3756
See application file for complete search history.

(56) References Cited

U.S. PATENT DOCUMENTS

| | | | |
|---|---|---|---|
| 6,913,614 | B2 | 7/2005 | Marino et al. |
| 7,011,671 | B2 | 3/2006 | Welch |
| 7,647,109 | B2 * | 1/2010 | Hastings .............. A61N 1/0587 607/32 |
| 8,615,310 | B2 | 12/2013 | Khairkhahan et al. |
| 8,958,892 | B2 | 2/2015 | Khairkhahan et al. |
| 2008/0283066 | A1 | 11/2008 | Delgado et al. |
| 2010/0268201 | A1 | 10/2010 | Tieu et al. |
| 2011/0270339 | A1 | 11/2011 | Murray, III et al. |
| 2013/0253345 | A1 | 9/2013 | Griswold et al. |
| 2014/0074114 | A1 | 3/2014 | Khairkhahan et al. |
| 2014/0142621 | A1 | 5/2014 | Masters et al. |
| 2015/0051611 | A1 | 2/2015 | Schmidt et al. |
| 2015/0051682 | A1 | 2/2015 | Schmidt et al. |

OTHER PUBLICATIONS

Ronan Wood, et al., Interventional Medical Systems and Associated Tethering Assemblies and Methods, U.S. Appl. No. 62/132,662, filed Mar. 13, 2015, 20pp.
Ronan Wood, Catheters for Deploying Implantable Medical Devices, and Associated Tethering Assemblies and Methods, U.S. Appl. No. 14/630,832, filed Feb. 25, 2015, 19pp.

* cited by examiner

*Primary Examiner* — George Manuel
(74) *Attorney, Agent, or Firm* — Evans M. Mburu (57) ABSTRACT

A tethering feature includes an elongate break-away member and a base, and forms a proximal end of an implantable medical device housing. A tether attachment zone of the break-away member extends between break-away member ends, and the base includes a pair of supports, wherein each end of the break-away member is wrapped around a corresponding support. A delivery catheter tether may be attached to the device tethering feature by passing a looped portion of the tether around the tether attachment zone. The device may be untethered from the catheter by applying a pull force through the attached tether, while a distal end of a shaft of the catheter, which abuts the device proximal end, provides a back-up force, the pull force unwrapping each end of break-away member from the corresponding base support.

15 Claims, 8 Drawing Sheets

INTERVENTIONAL MEDICAL SYSTEMS AND IMPLANTABLE MEDICAL DEVICES INCLUDING TETHERING FEATURES, AND ASSOCIATED METHODS

FIELD OF THE DISCLOSURE

The present disclosure pertains to interventional medical systems, and more particularly to tethering features of relatively compact implantable medical devices and associated methods.

BACKGROUND

Figure 1:
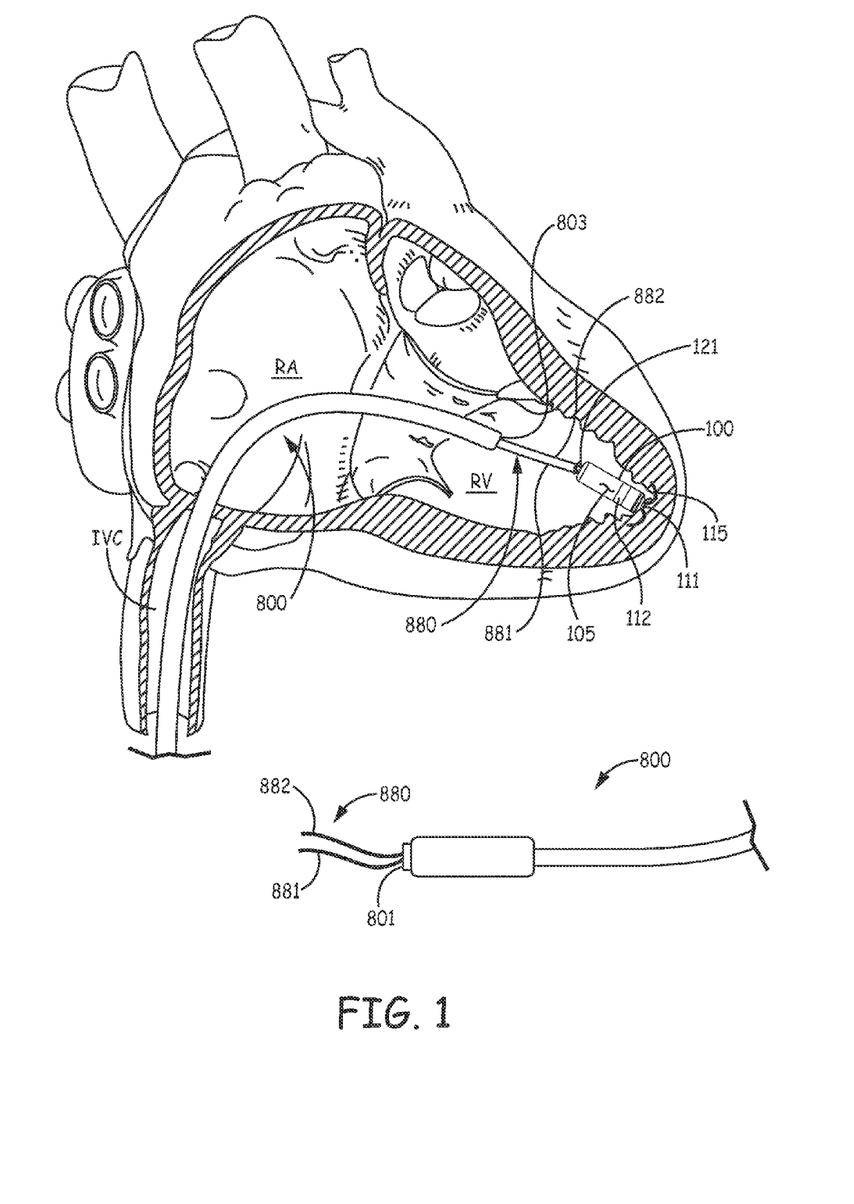
FIG. 1 is a schematic showing an exemplary implant of a relatively compact medical device, via an exemplary delivery catheter.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed housing 105, preferably formed from a biocompatible and biostable metal such as titanium, contains a pulse generator, or an electronic controller and associated power source (not shown), to which at least one electrode 111 is coupled, for example, by a hermetic feedthrough assembly (not shown) like those known to those skilled in the art. Housing 105 may be overlaid with an insulative layer, for example, medical grade polyurethane, parylene, or silicone, and a portion of the insulation layer may be removed to form another electrode 112, for example, which provides bipolar pacing and sensing in conjunction with electrode 111.

FIG. 1 shows device 100 having been deployed by an operator out from a distal opening 803 of a delivery catheter 800, which the operator has maneuvered up through the inferior vena cava IVC and the right atrium RA into the right ventricle RV. The deployed device 100 is shown fixed at an implant site by a fixation member 115 thereof, but still secured to catheter 800 by a tether 880 that extends out from distal opening 803 of catheter 800.

Securing device 100 to catheter 800 with tether 880 is typically accomplished, prior to maneuvering catheter 800, with device 100 loaded therein, to the illustrated site, by looping tether 880 through a tethering feature 121 of device 100 and threading first and second lengths 881, 882 of tether 880 through one or more lumens of catheter 800 such that opposing ends thereof protrude out from a proximal opening 801 of catheter 800. After deploying device 100, the operator can grasp the ends of lengths 881, 882, for example, to tug on tether 880 to test the fixation of device 100 at the implant site, and/or to apply a greater force to tether 880 to remove device 100 from the implant site for repositioning at a more suitable site, if necessary. If satisfied with the implant of device 100, the operator can remove the looped tether 880 from engagement with device 100 by releasing, for example, the end of length 881, and then pulling on the end of the other length 882, thereby withdrawing an entirety of length 882 proximally through delivery catheter 800 so that the other length 881 is pulled distally and through device tether tethering feature 121, out from engagement therewith.

SUMMARY

Embodiments and methods of the present disclosure pertain to improved tethering of relatively compact implantable medical devices in the context of deploying the devices to an implant site via a delivery catheter, for example, to increase the ease of tethering the devices and/or untethering, or releasing the devices, after deployment, from the delivery catheter.

According to some embodiments, a tethering feature of an implantable medical device forms a proximal end of a hermetically sealed housing that contains an electronic controller and an associated power source of the device, wherein the tethering feature includes an elongate break-away member and a base. The break-away member includes ends between which a tether attachment zone of the break-away member extends; and the base includes a pair of supports, wherein each end of the break-away member is wrapped around a corresponding support According to some embodiments and methods, an interventional medical system is formed by attaching a tether of a delivery catheter to the device tethering feature to tether the device to catheter, for example, with the aid of a needle-like member. After an operator manipulates the delivery catheter of the system to deploy the tethered device at an implant site, for example, so that a fixation member of the device engages tissue at the site, the operator may untether the device from the catheter by applying a pull force to the tether, while a distal end of a shaft of the catheter abuts the device tethering feature to provide a back-up force, thereby unwrapping the ends of the break-away member from the base supports.

BRIEF DESCRIPTION OF THE DRAWINGS

The following drawings are illustrative of particular embodiments of the present invention, and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
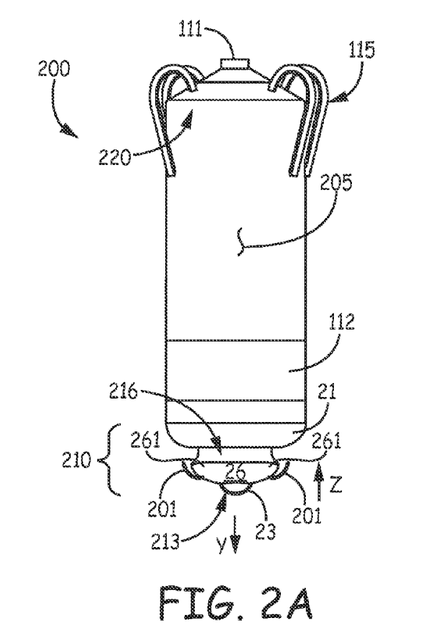
FIG. 2A is a plan view of an implantable medical device including a tethering feature, according to some embodiments.
Figure 2B:
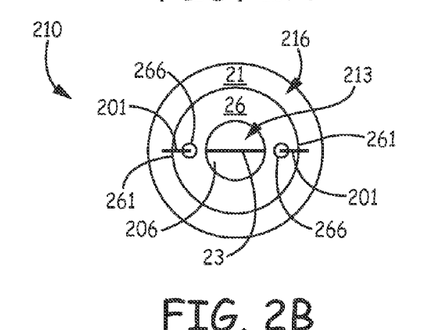
FIG. 2B is an end view of the device tethering feature shown in FIG. 2A, according to some embodiments.

FIG. 2A is a plan view of an implantable medical device 200 including a tethering feature 210 that forms a proximal end of a hermetically sealed housing 205 of device 200, according to some embodiments; and FIG. 2B is an end view of device tethering feature 210, according to some embodiments. FIGS. 2A-B illustrate tethering feature 210 including an elongate break-away member 213 and a base 216; break-away member 213 includes deformable ends 201, each of which is wrapped around a corresponding support 261 of base 216, and a tether attachment zone 23 that extends between ends 201. FIG. 2B shows each base support 261 formed by an edge of a corresponding aperture 266 that extends through a rim 26 of base 216, wherein rim 26 surrounds an open cavity 206 of base 216, which is spanned by tether attachment zone 23 of break-away member 213. According to the illustrated embodiment, each end 201 of break-away member 213 is configured to deform and unwrap from around the corresponding base support 261, thereby allowing break-away member 213 to separate from base 216 of tethering feature 210, when a pull force, per arrow Y of FIG. 2A, is applied to tether attachment zone 23, for example, by a tether 980 (FIGS. 7A-B), while a back-up force, per arrow Z of FIG. 2A, is applied to the proximal end of housing 205, for example, by a catheter shaft 520 that abuts base 216, which is described below in conjunction with FIG. 7A. Break-away member 213 may be formed from a medical grade metal, for example, being a Nitinol or Titanium wire, round (e.g., approximately 0.007 inch diameter cross-section) or ribbon (e.g., approximately 0.005 inch by approximately 0.012 inch cross-section).

FIG. 2A further illustrates device 200 including electrodes 111, 112 and fixation member 115, similar to device 100 introduced above in conjunction with FIG. 1. Electrode 111 is shown mounted to housing 205, for example, at a distal end 220 thereof, and is electrically coupled, for example, by a hermetically sealed feedthrough assembly known in the art, to the aforementioned electronic controller (not shown) that is hermetically sealed within housing 205. Fixation member 115 is shown including a plurality of fixation fingers mounted around a perimeter of housing distal end 220, for example, having been cut from Nitinol tubing, according to methods known in the art, and mounted to distal end 220 in a manner similar to that described for a fixation component in co-pending and commonly assigned United States Patent Application US 2012/0172690. Housing 205, like housing 105 of device 100, is preferably formed from a biocompatible and biostable metal such as titanium overlaid with an insulative layer, for example, medical grade polyurethane, parylene, or silicone, and a portion of the insulation layer may be removed to form electrode 112 as described above for device 100.

Figure 2C:
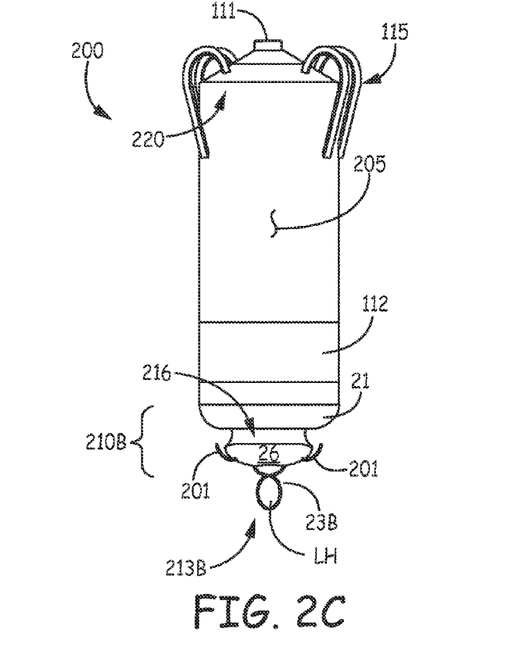
FIG. 2C is a plan view of the device including a tethering feature, according to some alternate embodiments.

FIG. 2C is a plan view of device 200 including a tethering feature 210B, according to some alternate embodiments. FIG. 2C illustrates tethering feature 210B including base 216, like feature 210, and an elongate break-away member 213B, which is similar to break-way member 213 except that a tether attachment zone 23B of member 213B forms a loophole LH. Zone 23B may simply be twisted to form loophole LH, for example, with more than two twists to prevent untwisting, or twisted and welded, or crimped, to form loophole LH. As described in greater detail below, when a tether, for example, tether 880 or 980 (FIG. 5B), is looped around tether attachment zone 23B of break-away member 213B, by extending through loophole LH, break-away member 213B can remain captured by the tether after the above-described applied forces unwrap ends 201 of break-away member 213B to separate member 213B from base 216 of device tethering feature 210B. With reference back to FIG. 2A, when a tether looped around break-away member 213 of tethering feature 210 unwraps ends 201 to separate member 213 from base 216 of device tethering feature 210, break-away member 213 without loophole LH may need to be captured within a shaft of a delivery catheter through which the tether extends. However, in some alternate embodiments, one of ends 201 of break-away member 213 is permanently secured to base 216, for example, via laser welding, so that the above-described applied forces only unwrap one of ends 201 of break-away member 213 from the corresponding base support 261 thereby allowing only the tether to separate from device tethering feature 210.

Figure 3:
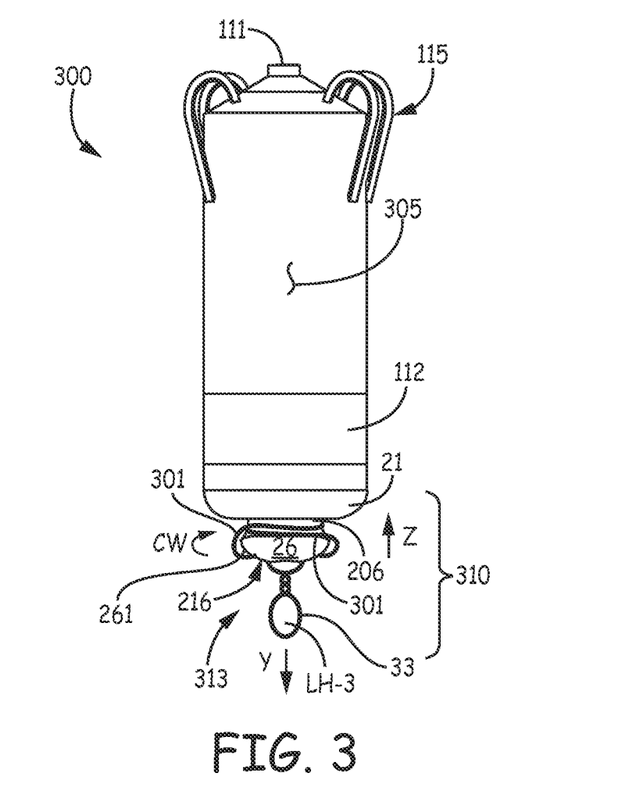
FIG. 3 is a plan view of an implantable medical device including a tethering feature, according to some additional embodiments.

FIG. 3 is a plan view of an implantable medical device 300, which is similar to device 200 except that device 300 includes a tethering feature 310, according to some additional embodiments. FIG. 3 illustrates tethering feature 310 forming a proximal end of a housing 305 of device 300, and including base 216, like tethering feature 210, and an elongate break-away member 313. Break-away member 313 is similar to break-away member 213B of tethering feature 210, except that deformable ends 301 of member 313 are longer than ends 201 of member 213B, such that each end 301 not only wraps around a corresponding base support 261 but also around a necked-in portion 206 of base 216, which extends between base rim 26 and a base distal shoulder 21. According to some preferred embodiments, break-away member ends 301 are both wrapped in the same direction around necked-in portion 206, for example, in a clockwise direction, per arrow CW of FIG. 3. FIG. 3 further illustrates break-away member 313 including a tether attachment zone 33, which extends between deformable ends 301 and forms a loophole LH-3. According to the illustrated embodiment, each end 301 of break-away member 313 is configured to deform and unwrap from around necked-in portion 206 and the corresponding base support 261, thereby allowing break-away member 313 to separate from base 216 of tethering feature 310, when a pull force, per arrow Y, is applied to tether attachment zone 33, for example, by tether 980, while a back-up force, per arrow Z, is applied to the proximal end of housing 305, for example, by catheter shaft 520 abutting base 216. According to an exemplary embodiments, break-away member 313 is formed from a medical grade metal, such as a round Titanium wire (e.g., approximately 0.005 inch diameter cross-section), and each end 301 of member 313 is approximately 3 cm long.

Figure 4A:
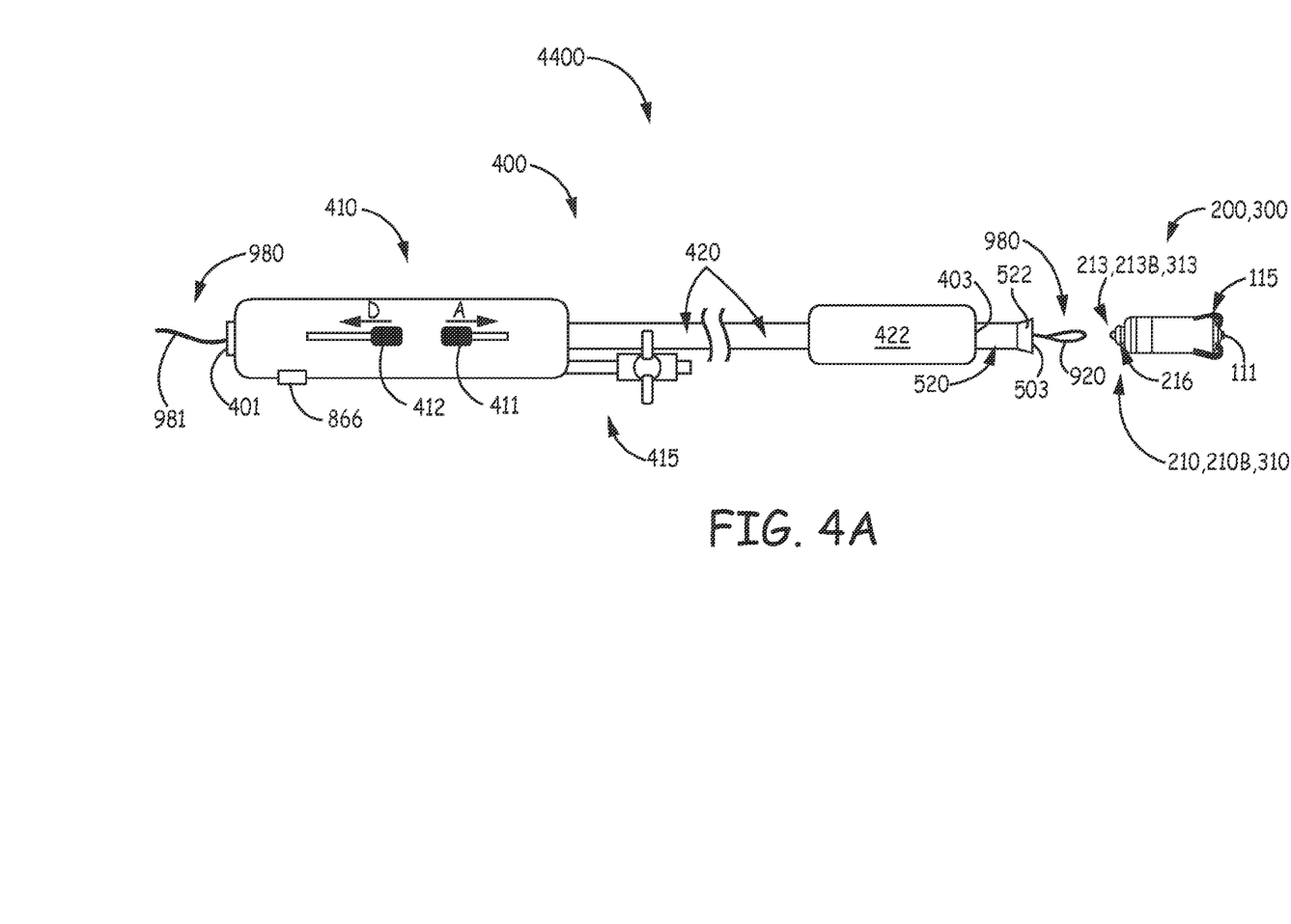
FIG. 4A is a plan view of an interventional medical system, according to some embodiments.

FIG. 4A is a plan view of an interventional medical system 4400, according to some embodiments. FIG. 4A illustrates system 4400 including an exemplary delivery catheter 400 and either of devices 200, 300, according to any of the embodiments described above, wherein device 200, 300 is positioned and oriented relative to catheter 400 for tethering thereto via tether 980. Delivery catheter 400 is shown including a handle assembly 410, a flushing assembly 415 coupled to handle assembly 410, an elongate outer tubular member 420, and an elongate flexible shaft 520, around which tubular member 420 is slideably engaged, and in which tether 980 extends. According to the illustrated embodiment, tether 980 extends within a lumen 502 of shaft 520 (seen in FIG. 6), so that a tether proximal end 981 extends out from a proximal port opening 401 of catheter 400 and a looped portion 920 of tether 980 extends out from a distal opening 503 of shaft lumen 502. According to some embodiments, system 4400 further includes a needle-like member 925 (shown in FIGS. 5A-B) temporarily secured to tether loop 920 and useful, according to some methods, for attaching looped portion 920 to device tethering feature 210, 210B, 310, for example, as described below in conjunction with FIGS. 5A-B. It should be noted that tether 880, as introduced above in conjunction with FIG. 1, may be employed in lieu of tether 980, according to some alternate embodiments. Furthermore, in some alternate embodiments, tether 980 does not include looped portion 920 until tether 980 is attached to break-away member 213, 213B, 313 of device tethering feature 210, 310, for example, by passing an end of tether 980 between break-away member 213, 213B, 313 and tethering feature base 216 and then securing the end to a remainder of tether 980 to form looped portion 920, such that looped portion 920 extends around tether attachment zone 23, 23B, 33 of break-away member 213, 213B, 313.

Figure 6:
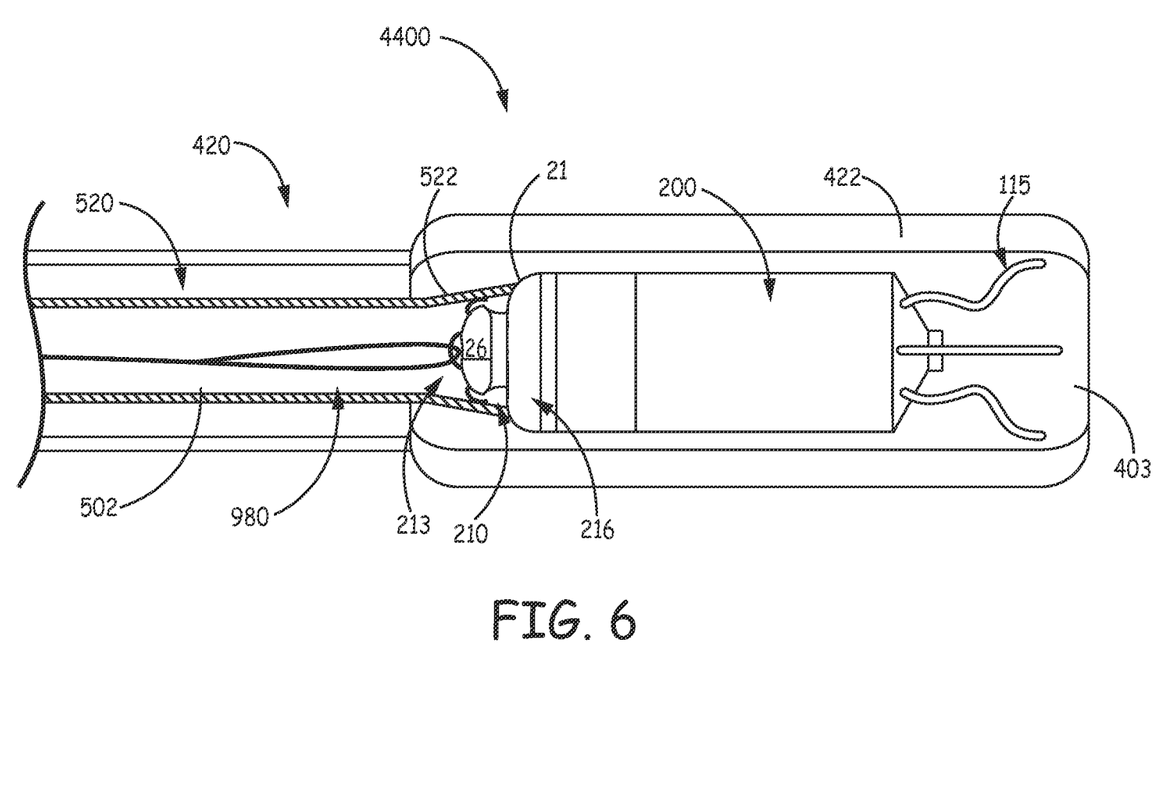
FIG. 6 is a cross-section view of a distal portion of the interventional medical system, according to some embodiments.

With further reference to FIG. 4A, a distal-most portion 422 of outer tubular member 420 is shown defining a distal opening 403 thereof, wherein distal-most portion 422 is sized to contain device 200, 300 for deployment thereof, as seen in FIG. 6. Outer tubular member 420 is shown retracted relative to shaft 520, for example, by moving a control member 411 of handle assembly 410 proximally, so that device 200, 300 can be tethered to catheter 400 prior to a loading thereof into distal-most portion 422, as described below. Delivery catheter 400 may also include a pull wire (not shown) that extends along a length of shaft 520 from a proximal end, which is coupled to another control member 412 of handle assembly 410, to a distal end, which is anchored in proximity to a distal end 522 of shaft 520. (According to some preferred embodiments, which are described below in conjunction with FIG. 7A, the anchor location for the option pull wire is located proximal to a relatively more flexible distal section of shaft 520 that extends adjacent to distal end 522.) Movement of control member 412, for example, per arrow D, actuates the pull wire to deflect shaft 520 and outer tubular member 420, which deflection may help an operator in maneuvering delivery catheter 400 to an implant site. FIG. 4A further illustrates shaft distal end 522 being enlarged from a remainder of shaft 520, according to some preferred embodiments, wherein distal end 522 is configured to surround break-away member tether attachment zone 23, 23B, 33 of device tethering feature 210, 210B, 310, when device 200, 300 is tethered to catheter 400, for example, as shown in FIG. 6 for tethering feature 210. Exemplary delivery catheter 400 may be constructed generally according to the detailed description of a similar catheter provided in a commonly assigned United States Patent Application US 2015/0094668, which has the Ser. No. 14/039,937.

Figure 4B:
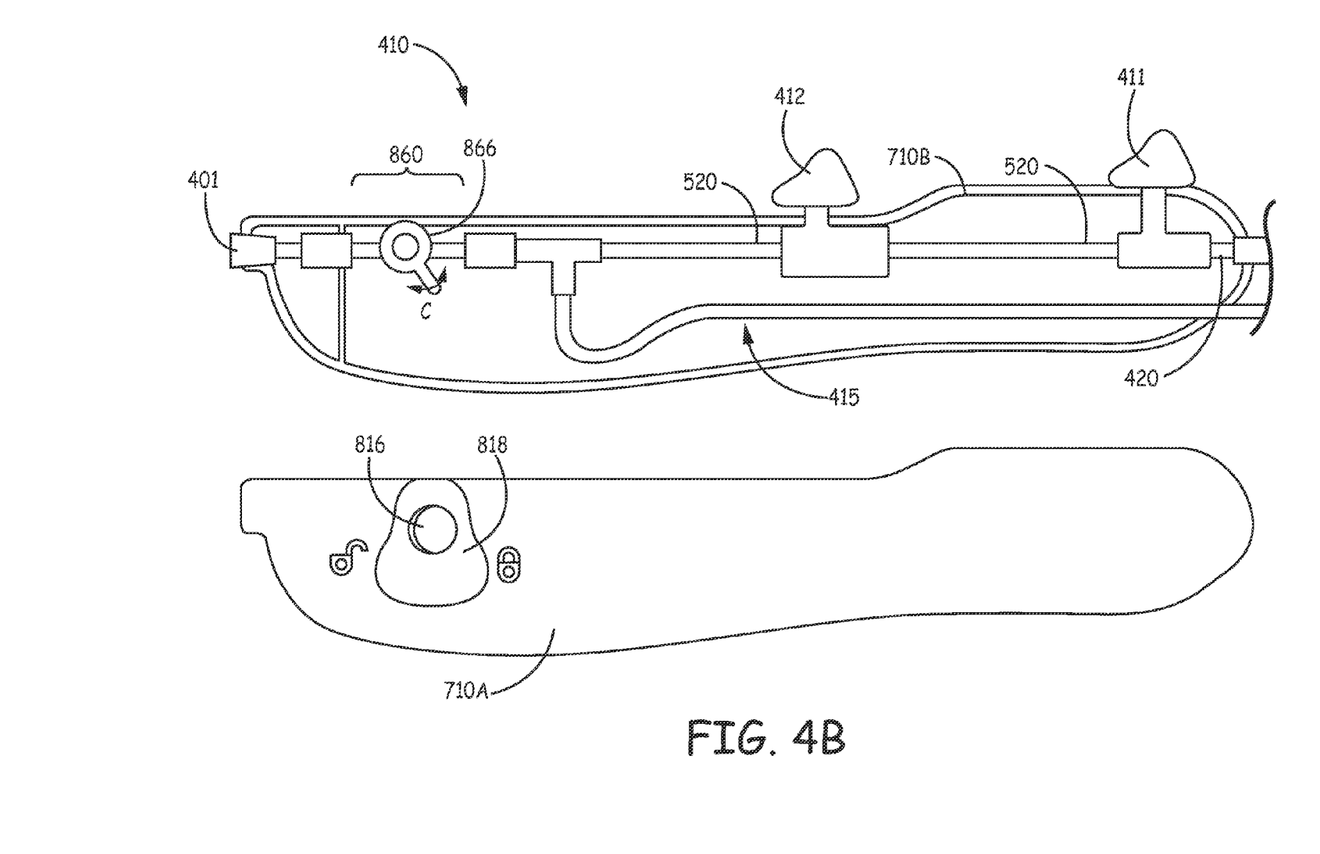
FIG. 4B is a plan view of an internal configuration of a handle assembly for an exemplary catheter of the system shown in FIG. 4A, according to some embodiments.

According to an exemplary embodiment, tether 980 is formed from a polyester fiber having a fluoropolymer coating, such as PTFE, and a proximal portion of tether 980 can be clamped within handle assembly 410 via actuation of a knob 866 of a valve member 860 that is integrated into a conduit of handle assembly 410, for example, as shown in FIG. 4B. FIG. 4B is a plan view of an internal configuration of handle assembly 410 wherein a first portion of an outer surface, or shell 710A of handle assembly 410 is removed to see an arrangement of components within a second portion of the shell 710B. According to an exemplary embodiment, valve member 860 is constructed like a stop-cock valve known to those skilled in the art, and first portion of shell 710A includes an aperture 816 formed through a recessed surface 818 thereof, which provides access to knob 866 of valve member 860, so that the operator can rotate knob 866 between an open position and a closed position, per arrow C. The open position allows free movement of tether 980 within shaft 520, while the closed position clamps down on the proximal portion of tether 980.

Figure 5A:
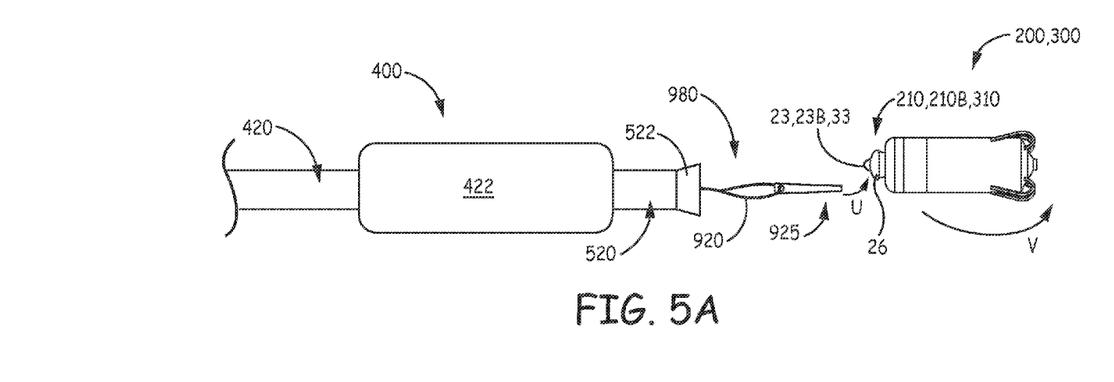
FIGS. 5A-B are schematics depicting steps of some methods for tethering the device of FIG. 2A to a delivery catheter of the system.
Figure 5B:
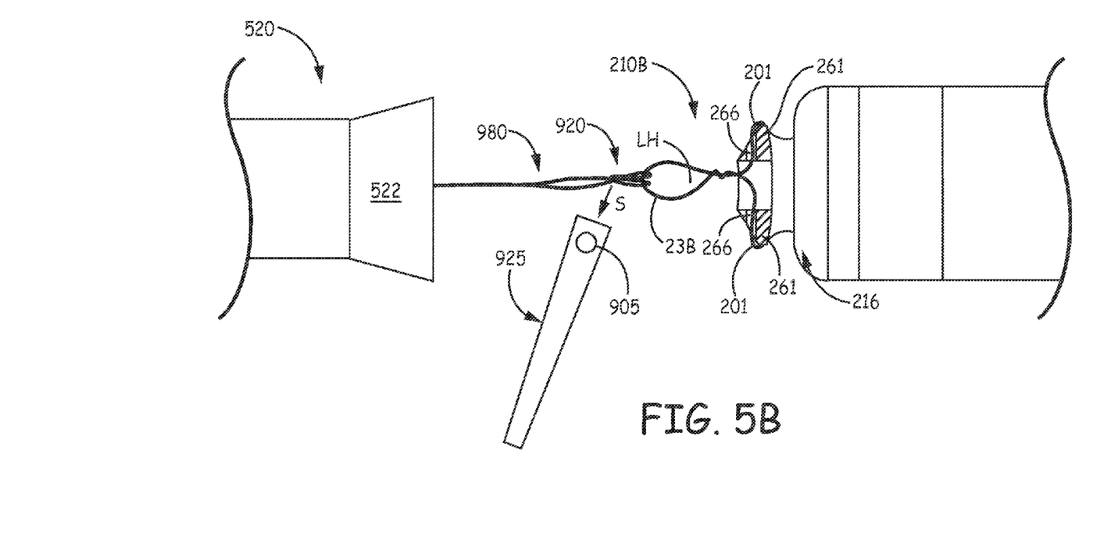

FIGS. 5A-B are schematics depicting steps of some methods for tethering device 200, 300 to delivery catheter 400. FIG. 5A illustrates the aforementioned optional needle-like member 925 temporarily secured to looped portion 920 of tether 980 to assist the operator in attaching tether 980 to device tethering feature 210, 210B, 310. Likewise, needle-like member 925 may be secured to tether 880, if employed in lieu of tether 980. According to some methods that employ needle-like member 925, the operator first inserts member 925 between break-away member tether attachment zone 23, 23B, 33 and tethering feature base 216, per arrow U, and then pulls looped portion 920 around device 200, 300, per arrow V, whereby looped portion 920 is passed around tether attachment zone 23, 23B, 33 to form a knot thereabout, for example, a girth hitch type knot, which is shown for tethering feature 210B in FIG. 5B. FIG. 5B further illustrates needle-like member 925 having been separated, per arrow S, from tether loop 920 after the knot is formed. According to some embodiments, member 925 may be formed from a relatively rigid medical grade plastic, and include an eyelet feature 905 with a relatively small gap through which tether 980 can be pulled for the separation. It should be noted that, according to some alternative methods, the illustrated knot in tether loop 920 may be formed without needle-like member 925. Furthermore, in some alternative embodiments, tether loop 920 may be in the form of a clip which may be attached to tethering feature break-away member 213, 213B, 313 without the need for forming a knot.

Once device 200, 300 is tethered to catheter 400, the operator can load device 200, 300 into catheter 400, for example, by pulling proximal end 981 of tether 980, which extends out from proximal port opening 401 (FIG. 4A), to draw tethering feature 210, 210B, 310 into distal end 522 of shaft 520, and then the operator can advance outer tubular member 420 relative to shaft 520 and tethered device 200, 300, by moving control member 411 distally, per arrow A of FIG. 4A, so that distal-most portion 422 of tubular member 420 contains device 200, 300, for example, as shown for device 200 in the cross-section view of FIG. 6. With reference back to FIG. 1, catheter 400, with device 200 loaded therein, can be maneuvered by the operator up through the inferior vena cava IVC and into the right ventricle RV, from the right atrium RA, to approach an implant site. According to the illustrated embodiment of FIG. 6, advancing outer tubular member 420 over device 200 moves the plurality of fixation fingers of fixation member 115 from a relaxed condition (FIG. 4A) to an extended condition, wherein the extended condition shown in FIG. 6 allows for initial engagement of the fingers with tissue T, when the operator has positioned distal opening 403 of outer tubular member 420 in close proximity to the implant site, and then retracts tubular member 420 relative to shaft 520 and device 200, for example, as shown in FIG.

Figure 7A:
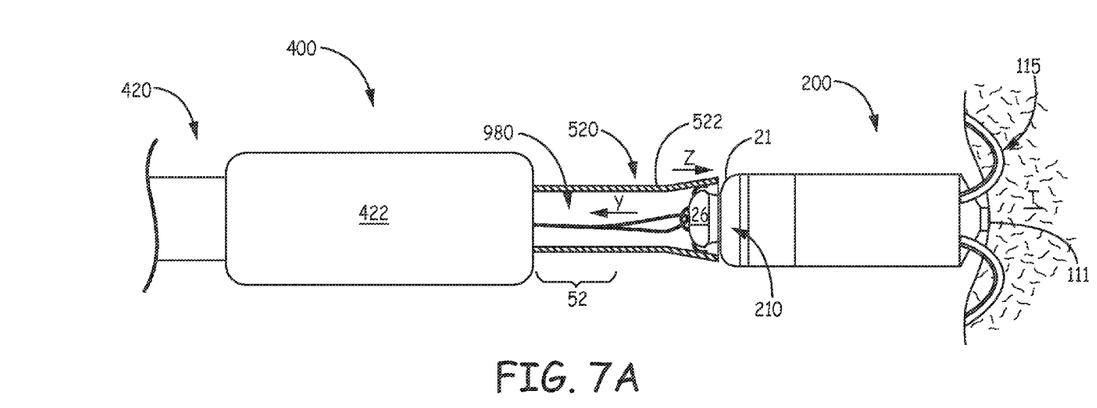
FIGS. 7A-B are schematics outlining some methods for untethering the device of FIG. 2A from the delivery catheter.

7A. According to some methods, the operator may evaluate the fixation of device 200 at the implant site by first withdrawing an entirety of catheter 400 proximally away from device 200, so that shaft distal end 522 no longer abuts tethering feature base 216 to apply the aforementioned back-up force, and then tugging on tether 980. Thus, a force necessary to unwrap break-away member ends 201 (without any back-up force) exceeds the holding force of fixation member 115 when sufficiently engaged with the tissue T.

Figure 7B:
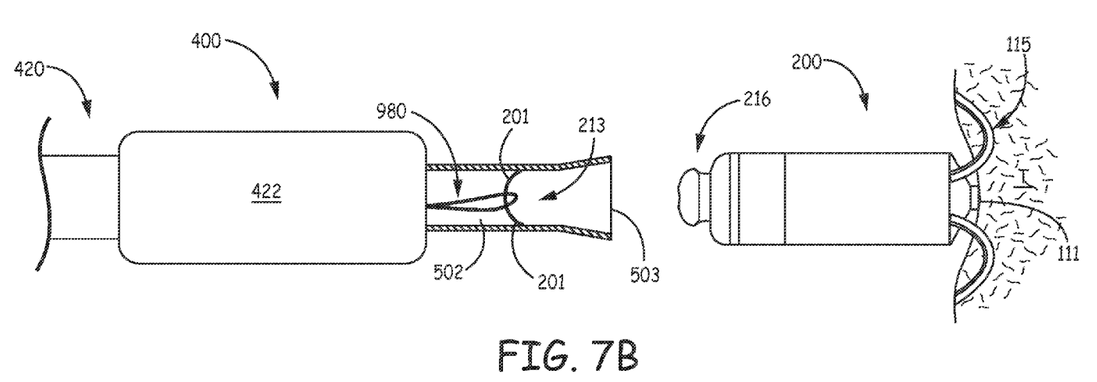

FIGS. 7A-B are schematics outlining some methods for untethering device 200 from delivery catheter 400, once device 200 is deployed at the implant site, for example, with fixation member 115 adequately engaged with tissue T. FIGS. 6 and 7A show enlarged distal end 522 of catheter shaft 520 surrounding break-away member 213 and abutting base 216 of device tethering feature 210, wherein shaft distal end 522 provides the above described back-up force, per arrow Z, for the above described pull force, per arrow Y, which is applied by the operator by pulling on tether proximal end 981 that extends out from proximal port opening 401 of catheter 400 (FIG. 4A). (FIGS. 6 and 7A show shaft distal end 522 extending to distal shoulder 21 of tethering feature base 116, but, in some alternate embodiments, distal end 522 only extends to rim 26 of base 216.) The simultaneous application of back-up and pull forces separates tethering feature break-away member 213 from base 216 of tethering feature 210, as described above in conjunction with FIGS. 2A-B, thereby untethering device 200 from catheter 400, for example, as shown in FIG. 7B. FIG. 7B illustrates the separated tethering feature break-away member 213 being secured to the catheter by a press fit of ends 201 within the shaft lumen 502, so that member 213 cannot slip out from tether loop 920. With reference back to FIGS. 2C, 3, and 5B, loophole LH of tethering feature 210B, or loophole LH-3 of tethering feature 310, secures separated break-away member 213B or 313 to tether 980 without the need for such a press fit within shaft lumen 502. It should also be noted that, according to the aforementioned alternate embodiments in which one end of break-away member 213, 213B, 313 is permanently secured to tethering feature base 216, 316, the break-away member remains implanted with the untethered device 200, 300.

In the case of tethering feature 210 (or 210B), according to the above-described exemplary embodiment of break-away member 213, the pull force applied to tether 980 (or 880) by the operator, to untether device 200, may be generally characterized by a rapid tug, or snap, over a relatively short distance; whereas, in the case of tethering feature 310, according to the above-described exemplary embodiment of break-away member 313, the operator applies the pull force over a greater distance to untether device 300, wherein the distance is proportional to a length of each end 301, and the pull force may be of a relatively lower magnitude and applied more slowly than the rapid tug. In any case, with further reference to FIG. 7A, according to some preferred embodiments, at least a distal section 52 of catheter shaft 520 is configured to flex freely in any direction, thereby allowing distal end 522 to align with device tethering feature 210, 310 at a variety of implant site locations. However, section 52 and distal end 522 preferably remains substantially incompressible to provide an effective back-up force to the pull force applied by the operator, through tether 980, when untethering device 200, 300.

In the foregoing detailed description, the invention has been described with reference to specific embodiments. However, it may be appreciated that various modifications and changes can be made without departing from the scope of the invention as set forth in the appended claims.

The invention claimed is:

1. An implantable medical device comprising an electronic controller and an associated power source, a hermetically sealed housing containing the controller and power source, an electrode electrically coupled to the controller and mounted to the housing, a fixation member mounted to a distal end of the housing, and an tethering feature forming a proximal end of the housing, wherein the tethering feature comprises:
   a elongate break-away member including deformable ends and a tether attachment zone extending between the ends; and
   a base including a pair of supports, each deformable end of the break-away member being wrapped around a corresponding support of the pair of supports and being configured to unwrap from the corresponding support when a pull force is applied, in a proximal direction, to the tether attachment zone while an opposing back-up force is applied to the proximal end of the device housing.

2. The device of claim 1, wherein the tether attachment zone of the tethering feature break-away member forms a loophole.

3. The device of claim 1, wherein each support of the tethering feature base comprises an edge of an aperture that extends through a rim of the base, the rim surrounding an open cavity of the base, and the cavity being spanned by the tether attachment zone of the tethering feature break-away member.

4. The device of claim 1, wherein:
   the tethering feature base further includes a proximal portion, a distal shoulder, and a necked-in portion that extends between the proximal portion and the distal shoulder; and
   each deformable end of the break-away member is also wrapped around the necked-in portion of the base.

5. An interventional medical system comprising an implantable medical device and a delivery catheter for deploying the device to an implant site; the device comprising an electronic controller and an associated power source, a hermetically sealed housing containing the controller and power source, an electrode electrically coupled to the controller and mounted to the housing, a fixation member mounted to a distal end of the housing, and an tethering feature forming a proximal end of the housing; the catheter comprising an elongate shaft and an elongate tether extending within a longitudinally extending lumen of the catheter shaft, a proximal end of the tether extending out from a proximal opening of the shaft lumen, and a looped portion of the tether extending out from a distal opening of the shaft lumen; and wherein:
   the catheter shaft includes a flexible distal length terminated by a distal end that defines the distal opening of the lumen, the distal end being configured to abut the proximal end of the tethered device housing; and
   the device tethering feature comprises:
      an elongate break-away member including deformable ends and a tether attachment zone extending between the ends; and
      a pair of supports, each deformable end of the break-away member being wrapped around a corresponding support of the pair of supports and being configured to unwrap from the corresponding support, when the tether of the catheter is attached to tether attachment zone of the break-away member, and when a pull force is applied to the tether to pull the tether attachment zone in a proximal direction while an opposing back-up force is applied by the distal end of the catheter shaft abutting the proximal end of the device housing.

6. The system of claim 5, wherein the distal end of the catheter shaft is enlarged and configured to surround the break-away member tether attachment zone of the device tethering feature.

7. The system of claim 6, wherein the tethering feature break-away member is configured so that, when the deformable ends are unwrapped, the break-away member separates from a remainder of the tethering feature and becomes secured to the catheter by a press fit within the shaft lumen.

8. The system of claim 5, wherein the delivery catheter further includes an elongate outer tubular member extending around the shaft in sliding engagement therewith, the outer tubular member including a distal-most portion sized to contain the tethered medical device therein.

9. The system of claim 5, further comprising a needle-like member temporarily secured to the looped portion of the tether of the catheter, the needle-like member being configured to pass the looped portion of the tether around the break-away member tether attachment zone of the device tethering feature, for attachment of the tether thereto, and then to be separated from the tether loop.

10. The system of claim 5, wherein the tether attachment zone of the break-away member of the device tethering feature forms a loophole.

11. The system of claim 5, wherein each support of the base of the device tethering feature comprises an edge of an aperture that extends through a rim of the base, the rim surrounding an open cavity of the base, and the cavity being spanned by the tether attachment zone of the tethering feature break-away member.

12. The system of claim 5, wherein:
the base of the device tethering feature further includes a proximal portion, a distal shoulder, and a necked-in portion that extends between the proximal portion and the distal shoulder; and
each end of the break-away member of the device tethering feature is also wrapped around the necked-in portion of the base.

13. A method for deploying a relatively compact implantable medical device to an implant site, the method comprising:
attaching a tether of a delivery catheter to a tethering feature of the device to tether the device to the catheter;
loading the tethered device into the delivery catheter such that a distal end of a shaft of the catheter abuts a tethering feature of the device and a distal-most portion of an outer tubular member of the catheter contains the device;
maneuvering the distal-most portion of the catheter with the tethered device loaded therein into proximity with the implant site;
retracting the outer tubular member of the catheter with respect to the catheter shaft to expose the device for engagement with tissue at the implant site, the outer tubular member being slideably engaged around the catheter shaft; and
unwrapping each end of a break-away member of the tethering feature of the engaged device from around a corresponding support of a base of the tethering feature by applying a pull force to the attached tether, thereby separating the break-away member and the tether from the engaged device, the pull force being backed up by the distal end of the catheter shaft abutting the device tethering feature.

14. The method of claim 13, further comprising pulling on the tether to secure the separated break-away member of the device tethering feature to the catheter by press fitting the separated break-away member within a lumen of the catheter shaft.

15. The method of claim 13, wherein attaching the delivery catheter tether to the device tethering feature comprises:
inserting a needle-like member between the tethering feature break-away member and the tethering feature base to pass a looped portion of the tether around the tether attachment zone of the break-away member; and
separating the needle-like member from the looped portion of the tether.

* * * * *